United States Patent
Jing et al.

(10) Patent No.: US 12,274,463 B2
(45) Date of Patent: Apr. 15, 2025

(54) SECTIONAL-TYPE THROMBUS EXTRACTION DEVICE

(71) Applicant: Hangzhou Exceed Medical Technology Co., Ltd, Hangzhou (CN)

(72) Inventors: Hongjuan Jing, Hangzhou (CN); Jiaping Huang, Hangzhou (CN)

(73) Assignee: Hangzhou Exceed Medical Technology Co., Ltd., Hangzhou (CN)

( * ) Notice: Subject to any disclaimer, the term of this patent is extended or adjusted under 35 U.S.C. 154(b) by 0 days.

(21) Appl. No.: 18/508,961

(22) Filed: Nov. 14, 2023

(65) Prior Publication Data

US 2024/0156479 A1 May 16, 2024

(30) Foreign Application Priority Data

Nov. 16, 2022 (CN) .......................... 2022114348645

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00778* (2013.01); *A61B 2017/22034* (2013.01); *A61B 2017/2212* (2013.01)

(58) Field of Classification Search
CPC ............ A61B 17/22031; A61B 17/221; A61B 2017/00778; A61B 2017/22034; A61B 2017/22035; A61B 2017/2212; A61B 2017/2215; A61B 2017/2217; A61F 2/82

USPC .......................................................... 606/159
See application file for complete search history.

(56) References Cited

U.S. PATENT DOCUMENTS

| | | | |
|---|---|---|---|
| 2013/0345739 A1* | 12/2013 | Brady ............ | A61B 17/320725 606/200 |
| 2015/0250497 A1* | 9/2015 | Marks .................. | A61B 17/221 606/159 |
| 2021/0045760 A1* | 2/2021 | Ulm, III ............ | A61M 25/0108 |
| 2021/0393277 A1* | 12/2021 | Vale .................. | A61M 25/0074 |

FOREIGN PATENT DOCUMENTS

CN          212788619 U      3/2021

* cited by examiner

*Primary Examiner* — Kankindi Rwego

(57) ABSTRACT

Disclosed is a thrombectomy device with segmented design, and the device includes a thrombectomy net and a push rod fixedly connected with a proximal end of the thrombectomy net, where the thrombectomy net is a tubular hollow self-expanding net capable of automatically expanding radially, which is contracted after being compressed radially, and expands radially after a constraint of radial compression is released. The thrombectomy net includes a slope section, a thrombectomy section, and a gathering section which are sequentially connected from the proximal end to a distal end, where the thrombectomy section includes at least two thrombectomy subsections which are sequentially connected from the proximal end to the distal end and are relatively independent, and two adjacent thrombectomy subsections are locally connected, so that the two adjacent thrombectomy subsections are relatively independent during radial expansion.

9 Claims, 4 Drawing Sheets

SECTIONAL-TYPE THROMBUS EXTRACTION DEVICE

CROSS-REFERENCE TO RELATED APPLICATIONS

This application claims priority from the Chinese patent application 2022114348645 filed Nov. 16, 2022, the content of which is incorporated herein in the entirety by reference.

TECHNICAL FIELD

The present disclosure relates to the technical field of medical devices, and particularly relates to a thrombectomy device with segmented design.

BACKGROUND

Acute ischemic stroke (AIS) is the most deadly ischemic cerebrovascular disease. Among stroke patients, AIS patients occupy a proportion of as high as 90%, followed by patients of cerebral arterial stenosis. AIS is caused by thrombotic or embolic occlusion of a cerebral artery and is characterized by a sudden loss of blood circulation in a part of the brain, which results in a corresponding loss of neurological function. AIS is characterized by high incidence, high disability, high mortality, and high recurrence.

Mechanical thrombectomy has the characteristics of a small trauma, a high recanalization rate, a reduced bleeding rate, and an extended therapeutic time window. A thrombectomy device is an interventional mechanical thrombectomy device. Specifically, the thrombectomy device is conveyed to a target lesion site through a microcatheter, and the thrombectomy device is released from the microcatheter and automatically expands radially. In the process of expansion radially, the thrombectomy device will be attached to a vascular wall after penetrating the thrombus so as to embed the thrombus. Then the thrombectomy device together with the thrombus will be sucked into a suction catheter, and taken out of the body of a patient with acute ischemic stroke, to restore blood flow in the body.

A Chinese invention patent CN106580397A discloses a thrombectomy device with segmented design, and the device includes a vascular thrombectomy stent and a conveying system connected to one end of the vascular thrombectomy stent, where the vascular thrombectomy stent is of a self-expandable net tube structure composed of a plurality of unit grids that are mutually connected. Radial clearances are formed in the net tube structure, and divide the net tube structure into a plurality of sectional structures that are sequentially connected, so that the radial expansion of each section is relatively independent, and the entire thrombectomy stent is attached to the vascular wall better. However, few connecting structures are arranged between the sections of the thrombectomy device, resulting in that the thrombus easily escapes from gaps between the sections, thus it is impossible to ensure rapid recanalization of an occluded blood vessel.

SUMMARY

In view of the above defects in the prior art, the present disclosure provides a thrombectomy device with segmented design to overcome the technical defects pointed out in the Background and solve the technical problem.

The present disclosure provides a thrombectomy device with segmented design, and the device includes a thrombectomy net and a push rod fixedly connected with a proximal end of the thrombectomy net, where the thrombectomy net is a tubular hollow self-expanding net capable of automatically expanding radially, which is contracted after being compressed radially, and expands radially after a constraint of radial compression is released. The thrombectomy net includes a slope section, a thrombectomy section, and a gathering section which are sequentially connected from the proximal end to a distal end, where the thrombectomy section includes at least two thrombectomy subsections which are sequentially connected from the proximal end to the distal end and are relatively independent, and two adjacent thrombectomy subsections of the at least two thrombectomy subsections are locally connected, so that the two adjacent thrombectomy subsections are relatively independent during radial expansion. Further, the two adjacent thrombectomy subsections are connected in an overlapping manner, so that a first double-layer net structure for preventing thrombi from escaping is formed at a joint.

Further, the distal end of each thrombectomy subsection is a tapered bell mouth, and the proximal end of one of the two adjacent thrombectomy subsections at the distal end extends into the tapered bell mouth at the distal end of the other thrombectomy subsection at the proximal end, and is enclosed with the tapered bell mouth to form the first double-layer net structure.

Further, the distal end of each thrombectomy subsection is provided with a plurality of petal-shaped net pieces, and the plurality of petal-shaped net pieces are distributed in a circumferential direction of an outer round surface of a corresponding thrombectomy subsection and form a tapered bell mouth at the distal end of the corresponding thrombectomy subsection.

Further, any two petal-shaped net pieces are not connected to each other.

Further, each petal-shaped net piece is in the shape of an arc, and a direction of the arc deviates from one side of a central axis of the thrombectomy subsection corresponding to the petal-shaped net piece.

Further, the plurality of petal-shaped net pieces are distributed in a direction of a spiral line in order from the proximal end to the distal end, and the spiral line is located on the outer round surface of the thrombectomy subsection corresponding to the plurality of petal-shaped net pieces.

Further, the gathering section is a tapered necking section that is opened at the proximal end and converged at the distal end, the distal end of the thrombectomy subsection located at the distal end of the thrombectomy section is connected to the proximal end of the gathering section, and the thrombectomy subsection is locally connected to the gathering section, so that the thrombectomy subsection and the gathering section are relatively independent during the radial expansion.

Further, the distal end of the thrombectomy subsection located at the distal end of the thrombectomy section is connected with the gathering section in an overlapping manner, to form a second double-layer net structure for preventing thrombi from escaping at the joint.

Further, an effective blocking area of the second double-layer net structure is larger than the effective blocking area of the first double-layer net structure.

Further, the slope section is a tapered flaring section that is converged at the proximal end and opened at the distal end, and the proximal end of the thrombectomy subsection located at the proximal end of the thrombectomy section is connected with the distal end of the slope section in a smooth transition manner.

Compared with the prior art, the present disclosure divides a thrombectomy section for embedding thrombus into at least two thrombectomy subsections that are sequentially connected and relatively independent, where the two adjacent thrombectomy subsections are locally connected, so that the two adjacent thrombectomy subsections are relatively independent during radial expansion, and each thrombectomy subsection is attached to the vascular wall well. Further, the two adjacent thrombectomy subsections are connected in an overlapping manner, so that the first double-layer net structure formed in this way can effectively prevent thrombus from escaping from a joint between two adjacent thrombectomy subsections, thus improving the success rate of thrombectomy and quickly recanalizing an occluded blood vessel.

BRIEF DESCRIPTION OF THE DRAWINGS

With reference to accompanying drawings and a detailed description below, the present disclosure and its accompanying advantages and features will be understood in an easier and more complete manner.

In the figures: 10, thrombectomy net; 11, slope section; 12, thrombectomy section; 121, thrombectomy subsection; 1211, petal-shaped net piece; and 13, gathering section.

It should be noted that the accompanying drawings are intended to illustrate the present disclosure, but not to limit the present disclosure. It should be noted that the accompanying drawings showing structures maybe are not drawn to scale. In the accompanying drawings, the same or similar elements are marked with the same or similar symbols.

DETAILED DESCRIPTION OF THE EMBODIMENTS

In order to make the content of the present disclosure clearer and easier to understand, a detailed description will be made below with reference to some specific embodiments and accompanying drawings.

A "proximal end" and a "distal end" referred to in the present disclosure should be understood as those observed from a direction of an attending doctor, where the "proximal end" refers to an end close to the attending doctor, and corresponds to a "left end" referred to in the accompanying drawings, while the "distal end" refers to an end away from the attending doctor, and corresponds to a "right end" referred to in the accompanying drawings.

Embodiment 1

Figure 6:
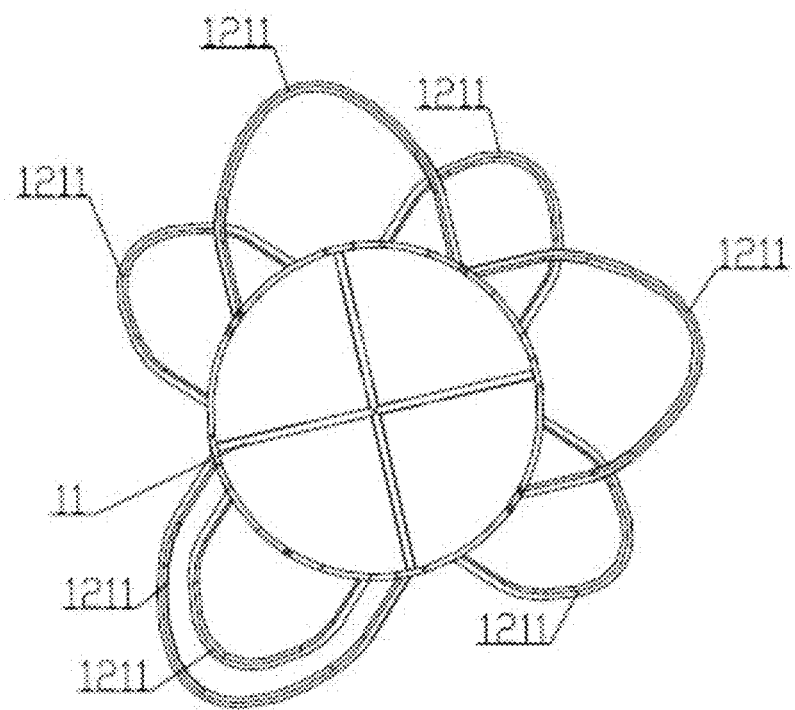
FIG. 6 is a left view of FIG. 1.
Figure 7:
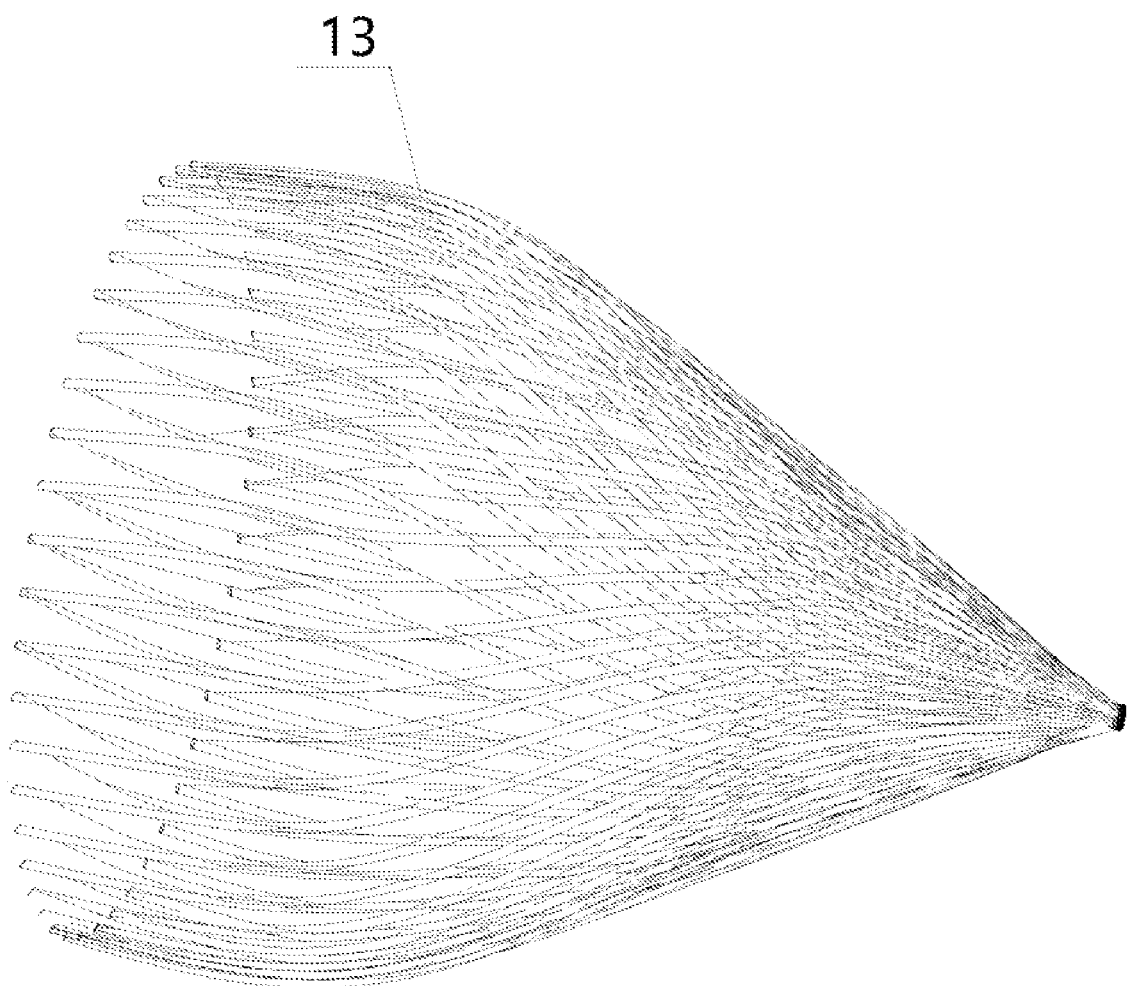
FIG. 7 is a schematic diagram of a structure of a gathering section in Embodiment 2 of the present disclosure.

A thrombectomy device with segmented design in this embodiment is an interventional device, which is conveyed through a microcatheter and released at a vascular lesion site for embedding thrombus. As shown in FIGS. 1-6, the thrombectomy device with segmented design includes a thrombectomy net 10 and a push rod (not shown), where the push rod is configured to convey the thrombectomy net 10 to a lesion site, a distal end of the push rod is fixedly connected with a proximal end of the thrombectomy net 10, a proximal end of the push rod and a distal end of the thrombectomy net 10 are both free ends, and the thrombectomy net 10 can be driven to move synchronously by pulling the push rod. The thrombectomy net 10 is a tubular hollow self-expanding net capable of automatically expanding radially, such as a metal net tube with memory performance, so that the thrombectomy net 10 is contracted after being compressed radially, and expands radially after a constraint of radial compression is released. As shown in FIGS. 7-9, during specific use, after the radially compressed thrombectomy net 10 is conveyed to a thrombus site in a blood vessel through a microcatheter, the microcatheter is withdrawn to release the thrombectomy net 10, and the released thrombectomy net 10 expands radially, and can be attached to an inner wall of the blood vessel after expansion. In the expansion process, the thrombectomy net 10 quickly embeds the thrombus through a plurality of net holes on its surface, and finally the push rod is pulled in a direction from the distal end to the proximal end to withdraw the thrombus-embedded thrombectomy net 10 into a suction catheter, so as to achieve recanalization of the blood vessel.

Figure 1:
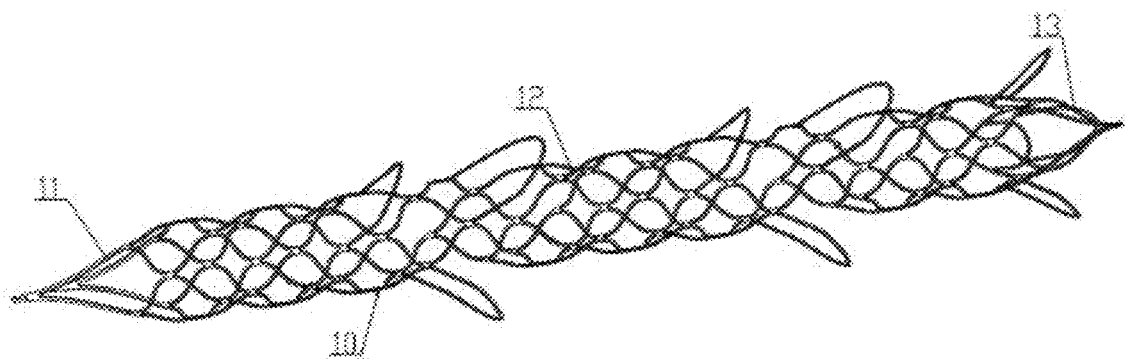
FIG. 1 is a schematic diagram of an overall structure of Embodiment 1 of the present disclosure.
Figure 2:
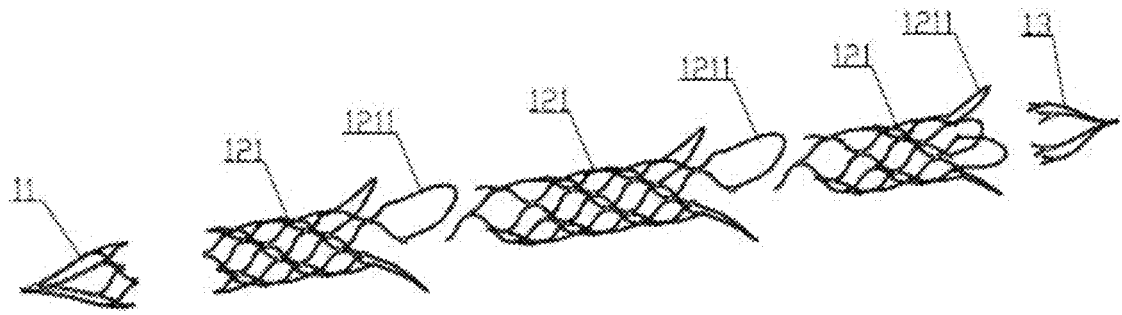
FIG. 2 is a schematic diagram of an explosive structure in FIG. 1.

As shown in FIGS. 1-2, the thrombectomy net 10 includes a slope section 11, a thrombectomy section 12, and a gathering section 13 that are sequentially connected from the proximal end to the distal end, where the thrombectomy section 12 includes at least two thrombectomy subsections 121 which are sequentially connected from the proximal end to the distal end and are relatively independent. The number of the thrombectomy subsections 121 in this embodiment is three, and the three thrombectomy subsections 121 are respectively located at the proximal end, the middle, and the distal end of the thrombectomy section 12. The entire thrombectomy section 12 formed by the three thrombectomy subsections 121 is configured to embed the thrombi. The slope section 11 is a tapered flaring section that is converged at the proximal end and opened at the distal end, and the proximal end of the thrombectomy subsection 121 located at the proximal end of the thrombectomy section 12 is connected with the distal end of the slope section 11 in a smooth transition manner. The slope section 11 belongs to a guide section, is configured mainly not to embed the thrombi, but to guide recovery of the thrombectomy net 10, and facilitates smooth recovery of the thrombectomy net 10 into the suction catheter after the thrombectomy. The gathering section 13 is a tapered necking section that is opened at the proximal end and converged at the distal end, the distal end of the thrombectomy subsection 121 located at the distal end of the thrombectomy section 12 is connected to the proximal end of the gathering section 13. The gathering section 13 belongs to an ending section, is configured mainly not to embed the thrombi, but to prevent the thrombi from escaping, and prevents the thrombi in the thrombectomy section 12 from escaping out of the thrombectomy net 10 from the distal end of the thrombectomy section 12 so as to avoid failure of the thrombectomy. It can be understood that, in other embodiments, the number of the thrombectomy subsections 121 can be set as two or more than three according to the specific amount of thrombus. Generally speaking, the number of the thrombectomy subsections 121 is not less than two.

Two adjacent thrombectomy subsections 121 are locally connected, that is, metal coverage of a connecting structure between two adjacent thrombectomy subsections 121 is low, resulting in that there are few connecting structures between the two adjacent thrombectomy subsections 121, so that the two adjacent thrombectomy subsections 121 are relatively independent during radial expansion, that is, the radial expansion of the thrombectomy subsection 121 at the proximal end will not affect the radial expansion of the thrombectomy subsection 121 in the middle, and the radial expansion of the thrombectomy subsection 121 in the middle will not affect the radial expansion of the thrombectomy subsection 121 at the distal end. In this way, neither a phenomenon that a certain thrombectomy subsection 121 cannot expand quickly due to a large amount of thrombus, which results in that another thrombectomy subsection 121 adjacent to this thrombectomy subsection 121 cannot expand smoothly and quickly to embed the thrombus and anchor the blood vessel, will occur, nor will a phenomenon that a certain thrombectomy subsection 121 cannot expand due to its own failure, which results in that another thrombectomy subsection 121 adjacent to this thrombectomy subsection 121 cannot expand. As a result, the two adjacent thrombectomy subsections 121 can fully contact the inner wall of the blood vessel after release, and be attached to the vascular wall better, with independent thrombectomy achieved. Further, the two adjacent thrombectomy subsections 121 are connected in an overlapping manner, so that a first double-layer net structure for preventing thrombi from escaping is formed at a joint. The first double-layer net structure can effectively avoid the situation where independent expansion of the two adjacent thrombectomy subsections 121 makes the thrombi easily escape from the joint between the two adjacent thrombectomy subsections 121 when withdrawing the thrombectomy net 10, and the effect of the first double-layer net structure is more obvious at a bending location of the blood vessel. That is to say, the thrombectomy subsections 121 relatively independent to each other jointly form a segmented thrombectomy section 12, and a thrombus escape structure is arranged at a joint of each subsection, so that the success rate of thrombectomy is increased, and an occluded blood vessel can be quickly recanalized.

The distal end of each thrombectomy subsection 121 is a tapered bell mouth, and the proximal end of one of the two adjacent thrombectomy subsections 121 at the distal end extends into the tapered bell mouth at the distal end of the other thrombectomy subsection 121 at the proximal end, and is enclosed with the tapered bell mouth to form the first double-layer net structure. That is, an inner layer of the first double-layer net structure is formed at the proximal end of a thrombectomy subsection 121 at the distal end, and an outer layer of the first double-layer net structure is formed at the distal end of a thrombectomy subsection 121 at the proximal end, where the outer layer is in the shape of a bell mouth, so that at the bending location of the blood vessel, the outer layer is still attached to the vascular wall without constraint by the inner layer. Therefore, it can effectively prevent the thrombi from escaping.

Figure 3:
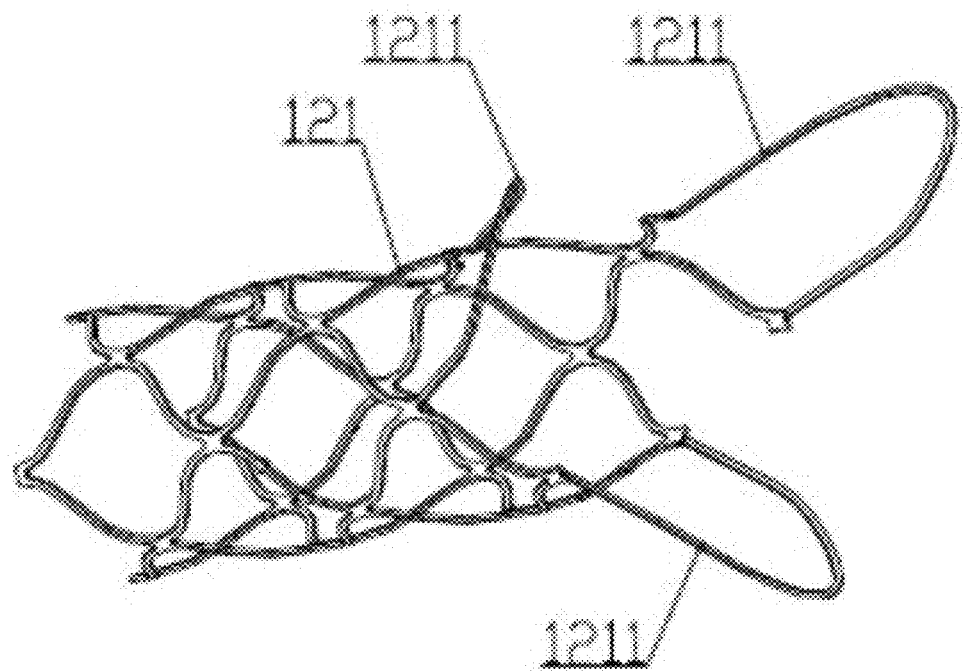
FIG. 3 is a schematic diagram of a structure of a thrombectomy subsection at a proximal end of a thrombectomy section in FIG. 2.
Figure 4:
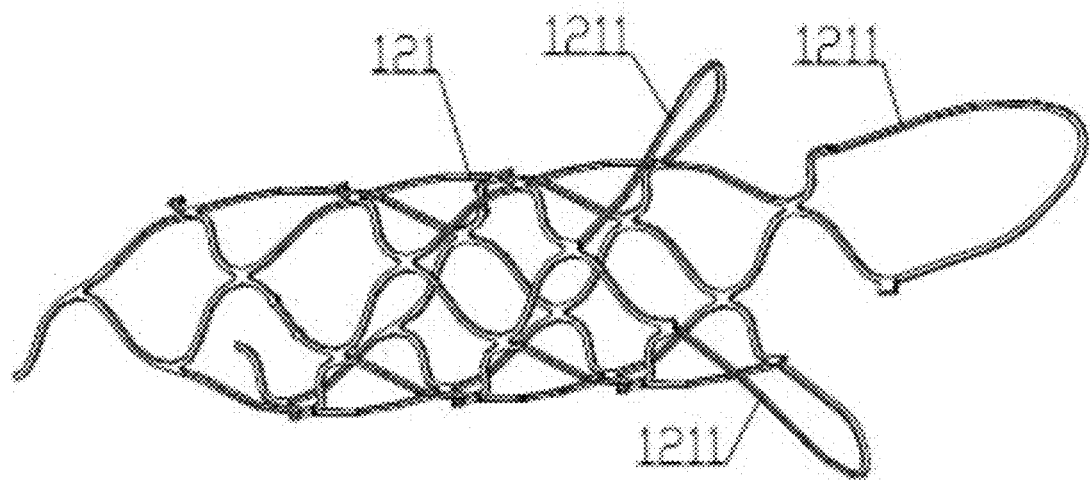
FIG. 4 is a schematic diagram of a structure of a thrombectomy subsection in the middle of the thrombectomy section in FIG. 2.
Figure 5:
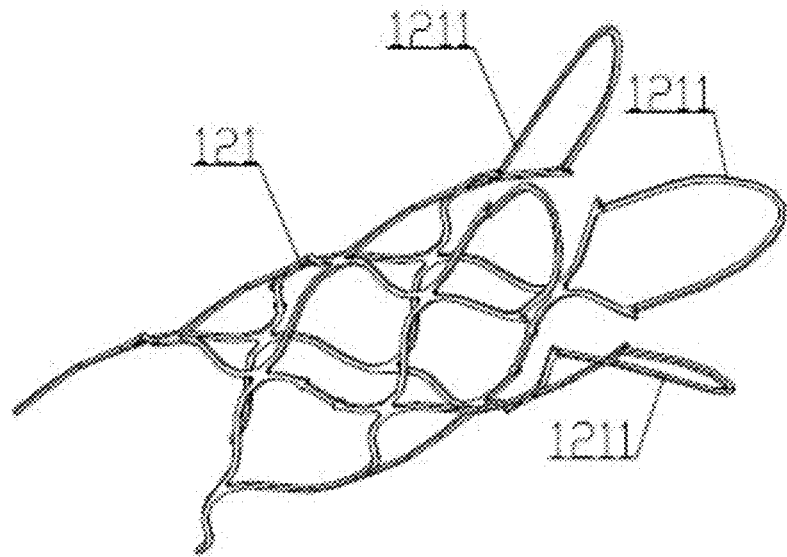
FIG. 5 is a schematic diagram of the structure of a thrombectomy subsection at a distal end of the thrombectomy section in FIG. 2.

As shown in FIGS. 3-5, the distal end of each thrombectomy subsection 121 is provided with a plurality of petal-shaped net pieces 1211, and the plurality of petal-shaped net pieces 1211 are distributed in a circumferential direction of an outer round surface of a corresponding thrombectomy subsection 121 and form a tapered bell mouth at the distal end of the corresponding thrombectomy subsection 121. Further, any two petal-shaped net pieces 1211 on a same thrombectomy subsection 121 are not connected to each other, and any one petal-shaped net piece 1211 on a thrombectomy subsection 121 is not connected to a proximal end of another adjacent thrombectomy section 121, that is, the connecting structure between the two adjacent thrombectomy subsections 121 is not directly connected to the plurality of petal-shaped net pieces 1211, so that each of the petal-shaped net pieces 1211 is a free net piece, which can be better attached to the inner wall of the blood vessel. The petal-shaped net pieces 1211 not only play a better role in attaching to the vascular wall, but also have the effect of forming the outer layer of the first double-layer net structure. In order to further enhance the attachment of each petal-shaped net piece 1211 to the vascular wall, each petal-shaped net piece 1211 is arranged to be in the shape of an arc in this embodiment, and a direction of the arc deviates from one side of a central axis of the thrombectomy subsection 121 corresponding to the petal-shaped net piece 1211, so that when the thrombectomy net 10 is withdrawn, in case that a thrombus escapes in a certain thrombectomy subsection 121, a petal-shaped net piece 1211 on another thrombectomy subsection 121 located at the distal end of the thrombectomy subsection 121 can be withdrawn together with the escaped thrombus, further resulting in that the thrombus enters the thrombectomy subsection 121 from the inner layer of the first double-layer net structure.

In this embodiment, the plurality of petal-shaped net pieces 1211 are distributed in the direction of a spiral line in order from the proximal end to the distal end, and the spiral line is located on the outer round surface of the thrombectomy subsection 121, that is, the plurality of petal-shaped net pieces 1211 on the thrombectomy subsection 121 at the proximal end of the thrombectomy section 12 are spirally distributed on the thrombectomy subsection 121, the advantage of which is that in an aspect, such distribution can give full play to the wall attachment of each petal-shaped net piece 1211, and is conducive to enhancing the wall attachment of the thrombectomy subsection 121; in a further aspect, such distribution can disperse an expansion force of the plurality of petal-shaped net pieces 1211 on the inner wall of the blood vessel, and is beneficial to reducing stimulation to the inner wall of the blood vessel; and in yet another aspect, such distribution enables each petal-shaped net piece 1211 to block the escaped thrombus from different coordinate points, and is beneficial to preventing further escape of the thrombus. Similarly, the plurality of petal-shaped net pieces 1211 on the thrombectomy subsection 121 located between the proximal end and the distal end of the thrombectomy section 12 are also spirally distributed on the thrombectomy subsection 121. That is to say, the plurality of petal-shaped net pieces 1211 on the thrombectomy subsections 121 other than the thrombectomy subsection 121 at the distal end of the thrombectomy section 12 are all spirally distributed on their respective thrombectomy subsections 121, while the plurality of petal-shaped net pieces 1211 on the thrombectomy subsection 121 at the distal end of the thrombectomy section 12 are annularly and evenly distributed on the same circumference of the outer round surface of the thrombectomy subsection 121. Such arrangement results in that a distribution interval between the petal-shaped net pieces 1211 on the thrombectomy subsection 121 at the distal end of the thrombectomy section 12 is shorter than that between the petal-shaped net pieces 1211 on the other thrombectomy subsections 121, so that it can serve as a last line of defense for preventing the thrombi from escaping. In order to further highlight this effect, as shown in FIG. 6, in this embodiment, the number of the petal-shaped net pieces 1211 on the thrombectomy subsection 121 at the distal end of the thrombectomy section 12 is set as four, while the number of the petal-shaped net pieces 1211 on each of the other thrombectomy subsections 121 is set as three, that is, the number of the petal-shaped net pieces 1211 on the thrombectomy subsection 121 at the distal end of the thrombectomy section 12 is larger than the number of the petal-shaped net pieces 1211 on each of the other thrombectomy subsections 121, the petal-shaped net pieces 1211 on other thrombectomy subsections 121 are arranged in one-to-one correspondence, and the petal-shaped net pieces 1211 on the thrombectomy subsection 121 at the distal end of the thrombectomy section 12 and the petal-shaped net pieces 1211 on the other thrombectomy subsections 121 are arranged in a staggered manner. It can be understood that in other embodiments, a plurality of petal-shaped net pieces 1211 on all thrombectomy subsections 121 can also be arranged to be distributed in a direction of a spiral line in order from a proximal end to a distal end, the spiral line is located at an outer round surface of the thrombectomy subsection 121 corresponding to the plurality of petal-shaped net pieces 1211, and the number of the petal-shaped net pieces 1211 on the thrombectomy subsection 121 at the distal end of the thrombectomy section 12 is made to be larger than the number of the petal-shaped net pieces 1211 on each of the other thrombectomy subsections 121.

In this embodiment, the proximal end of the gathering section 13 is locally connected with the distal end of the thrombectomy subsection 121 located at the distal end of the thrombectomy section 12, that is, the metal coverage of the connecting structure between the proximal end of the gathering section 13 and the distal end of the thrombectomy subsection 121 located at the distal end of the thrombectomy section 12 is low, resulting in that there are few connecting structures between the proximal end of the gathering section 13 and the distal end of the thrombectomy subsection 121 located at the distal end of the thrombectomy section 12, so that the gathering section 13 and the thrombectomy subsection 121 are relatively independent during the radial expansion, thus ensuring that the gathering section 13 as the last line of defense for preventing the thrombi from escaping is capable to radially expand in a relatively independent manner. Further, the gathering section 13 and the thrombectomy subsection 121 are connected in an overlapping manner, so that a second double-layer net structure is formed at the joint, and an effective blocking area of the second double-layer net structure is larger than the effective blocking area of the first double-layer net structure. In this way, the gathering section 13 is capable to radially expand in a relatively independent manner to open, and also has the denser second double-layer net structure, so that the gathering section 13 is capable to play its role as the last line of defense. The gathering section 13 is formed by gathering a plurality of gathering rods that can be made by cutting. The plurality of gathering rods are roughly parallel to each other, proximal ends of the plurality of gathering rods are scattered and connected to the distal end of the thrombectomy subsection 121 located at the distal end of the thrombectomy section 12, the connecting structure is not directly connected with the plurality of petal-shaped net pieces 1211 at the distal end of the thrombectomy subsection 121, the distal ends of the plurality of gathering rods are converged at one end point, and the distance between two adjacent gathering rods is small.

In this embodiment, as shown in FIG. 7, in an initial state in a specific process of thrombectomy, the thrombectomy net 10 is compressed in the microcatheter, and after the radially compressed thrombectomy net 10 is conveyed to a thrombus site in a blood vessel through the microcatheter the microcatheter is withdrawn to release the thrombectomy net 10. The gathering section 13 at the distal end of the thrombectomy net 10 is released first, and after the gathering section 13 is completely released, the plurality of petal-shaped net pieces 1211 on the thrombectomy subsection 121 at the distal end connected to the gathering section 13 quickly anchor the inner wall of the blood vessel as shown in FIG. 8, to prevent displacement of the entire thrombectomy net 10 and form the second double-layer net structure for preventing thrombi from escaping at the proximal end of the gathering section 13. Then the thrombectomy subsection 121 at the distal end connected to the gathering section 13 is completely released. After being completely released, the thrombectomy subsection 121 at the distal end quickly expands and contacts the inner wall of the blood vessel, without constraint by the unreleased thrombectomy subsection 121 in the middle. By analogy, the entire thrombectomy net 10 can be released. In the release process of the entire thrombectomy net 10, the gathering section 13 and each thrombectomy subsection 121 expand in a manually independent manner and contact with the inner wall of the blood vessel to achieve attachment to the vascular wall, so that the entire thrombectomy net 10 will not be moved, but is capable to quickly embed the thrombus in the blood vessel. Therefore, the effect of embedding the thrombus is excellent, and the time of standing still in the blood vessel is also short, such that the thrombectomy net 10 can be withdrawn from the blood vessel in a shorter period of time. A schematic diagram of the thrombectomy net 10 withdrawn from the blood vessel and the thrombus embedded in the thrombectomy net 10.

The following table shows the clinical control data of the thrombectomy net 10 in this embodiment. In this embodiment, a 100% success rate of recanalization of target vessels can be achieved, that is, vascular recanalization can be achieved for every thrombectomy. Specifically, vascular recanalization rates of control groups 1 and 2 are 90.7% and 92.3%, respectively. Here, the vascular recanalization refers to reflow of blood in blood vessels of a patient after the thrombectomy. When the reflow of the blood in blood vessels of N of M patients is finally achieved after the thrombectomy, the success rate of recanalization of target vessels is N/M.

|  | This embodiment | Control group 1 | Control group 2 |
| --- | --- | --- | --- |
| Success rate of recanalization of target vessels | 100% | 90.7% | 92.3% |

Further, for the thrombectomy, vascular recanalization should be achieved through reduction of thrombectomy times as much as possible. Therefore, the first-attempt recanalization rate is crucial for the effect of thrombectomy. In this embodiment, the first-attempt recanalization rate is as high as 66.7%. However, an average first-attempt recanalization rate of existing control groups is only 44.35%, which means that the existing control products usually require two or more thrombectomy times to achieve vascular recanalization.

Embodiment 2

As shown in FIG. 7., this embodiment is different from the Embodiment 1 in that a plurality of gathering rods of a gathering section 13 of this embodiment are intersected to form a denser gathering structure, and the gathering section 13 may be made by weaving. Other structures of this embodiment are the same as those of the Embodiment 1, and details are not described herein again.

It can be understood that although the present disclosure has been disclosed above with preferred embodiments, the above embodiments are not intended to limit the present disclosure. Any person skilled in the art, without departing from the scope of the technical solution of the present invention, may take many possible changes and modifications to the technical solution of the present disclosure by using the above disclosed methods and technical contents, or modify the technical solution of the present disclosure into equivalent embodiments with equivalent changes. Therefore, any simple alteration, equivalent change and modification which are made to the above embodiments in accordance with the technical essence of the present invention without departing from the contents of the technical solutions of the present invention all fall within the scope of protection of the technical solution of the present invention.

The invention claimed is:

1. A thrombectomy device with segmented design, comprising a thrombectomy net (10) and a push rod fixedly connected with a proximal end of the thrombectomy net (10), wherein the thrombectomy net (10) is a tubular hollow self-expanding net capable of automatically expanding radially, which is contracted after being compressed radially, and expands radially after a constraint of radial compression is released; the thrombectomy net (10) comprises a slope section (11), a thrombectomy section (12), and a gathering section (13) which are sequentially connected from the proximal end to a distal end, wherein the thrombectomy section (12) comprises at least two thrombectomy subsections (121) which are sequentially connected from the proximal end to the distal end and are relatively independent, and two adjacent thrombectomy subsections (121) of the at least two thrombectomy subsections are locally connected, so that the two adjacent thrombectomy subsections (121) are relatively independent during radial expansion;

and further, a distal end of each thrombectomy subsection (121) of the two adjacent thrombectomy subsections (121) is a tapered bell mouth, and the two adjacent thrombectomy subsections (121) are a directly overlapped connection along the circumference of a second tapered bell mouth;

and a proximal end of a first of the two adjacent thrombectomy subsections (121) at the distal end of the thrombectomy net (10) extends into the second tapered bell mouth at a distal end of a second of the two adjacent thrombectomy subsections (121) at the proximal end of the thrombectomy net (10), and is enclosed within the second tapered bell mouth to form a first double-layer net structure, so that the first double-layer net structure for preventing thrombi from escaping is formed at a first joint.

2. The thrombectomy device with segmented design according to claim 1, wherein the distal end of each thrombectomy subsection (121) of the two adjacent thrombectomy subsections (121) is provided with a plurality of petal-shaped net pieces (1211), and the plurality of petal-shaped net pieces (1211) are distributed in a circumferential direction of an outer round surface of a corresponding one of the two adjacent thrombectomy subsections (121) and form the tapered bell mouth at a distal end of the corresponding one of the two adjacent thrombectomy subsections (121).

3. The thrombectomy device with segmented design according to claim 2, wherein any two petal-shaped net pieces are not connected to each other, and each of the petal-shaped net pieces (1211) is a free net piece.

4. The thrombectomy device with segmented design according to claim 2, wherein each petal-shaped net piece (1211) is in the shape of an arc, and a direction of the arc deviates from one side of a central axis of the thrombectomy subsection (121) corresponding to the petal-shaped net piece (1211).

5. The thrombectomy device with segmented design according to claim 2, wherein the plurality of petal-shaped net pieces (1211) in the distal end of each thrombectomy subsection (121) of the two adjacent thrombectomy subsections (121) are distributed in the direction of a spiral line in order from the proximal end to the distal end, and the spiral line is located on the outer round surface of the thrombectomy subsection (121) corresponding to the plurality of petal-shaped net pieces (1211).

6. The thrombectomy device with segmented design according to claim 1, wherein the gathering section (13) is a tapered necking section that is opened at the proximal end and converged at the distal end, a first thrombectomy subsection (121) at the distal end of the thrombectomy net (10) is connected to the proximal end of the gathering section (13), and the first thrombectomy subsection (121) is locally connected to the gathering section (13), so that the first thrombectomy subsection (121) and the gathering section (13) are relatively independent during the radial expansion.

7. The thrombectomy device with segmented design according to claim 6, wherein the first thrombectomy subsection (121) is connected with the gathering section (13) in an overlapping manner, to form a second double-layer net structure for preventing thrombi from escaping at a second joint.

8. The thrombectomy device with segmented design according to claim 7, wherein an effective blocking area of the second double-layer net structure is larger than an effective blocking area of the first double-layer net structure.

9. The thrombectomy device with segmented design according to claim 1, wherein the slope section (11) is a tapered flaring section that is converged at the proximal end and opened at the distal end, and a third thrombectomy subsection (121) at the proximal end of the thrombectomy net (10) is connected with the distal end of the slope section (11) in a smooth transition manner.

* * * * *